United States Patent [19]

Cussler

[11] Patent Number: 4,957,620
[45] Date of Patent: Sep. 18, 1990

[54] LIQUID CHROMATOGRAPHY USING MICROPOROUS HOLLOW FIBERS

[75] Inventor: Edward L. Cussler, Edina, Minn.

[73] Assignee: Hoechst Celanese Corporation, Somerville, N.J.

[21] Appl. No.: 271,449

[22] Filed: Nov. 15, 1988

[51] Int. Cl.$^5$ .............................................. B01D 15/08
[52] U.S. Cl. ..................................... 210/635; 210/656; 210/198.2; 210/502.1; 210/500.23; 55/67; 55/386
[58] Field of Search ............ 210/635, 656, 658, 198.2, 210/502.1, 500.23; 55/386, 67

[56] References Cited

U.S. PATENT DOCUMENTS

| | | | |
|---|---|---|---|
| 2,106,744 | 2/1938 | Hood et al. | 186/26.1 |
| 2,334,961 | 11/1943 | Schoenlaub | 106/50 |
| 2,571,074 | 10/1951 | Tiede et al. | 106/50 |
| 3,082,614 | 3/1963 | Denniston | 65/3 |
| 3,268,313 | 8/1966 | Burgman et al. | 161/178 |
| 3,442,002 | 5/1969 | Geary, Jr. et al. | 29/45 X |
| 3,510,393 | 5/1970 | Burgman et al. | 65/5 |
| 3,570,673 | 3/1971 | Dutz et al. | 210/198.2 |
| 3,630,700 | 12/1971 | Hammond | 65/21 |
| 3,650,721 | 3/1972 | Hammel et al. | 65/31 |
| 3,737,042 | 6/1973 | Boom | 210/321 |
| 3,808,125 | 4/1972 | Good | 210/198.2 |
| 3,816,304 | 6/1974 | Wallis et al. | 210/36 |
| 3,847,626 | 11/1974 | Erickson et al. | 106/50 |
| 3,878,092 | 4/1975 | Fuller | 210/198.2 |
| 3,983,053 | 9/1976 | Courtney | 210/635 |
| 4,020,142 | 3/1977 | Davis et al. | 264/347 |
| 4,029,583 | 6/1977 | Chang et al. | 210/502 |
| 4,042,359 | 8/1977 | Schnabel et al. | 65/2 |
| 4,045,352 | 8/1977 | Rembaum | 210/500.23 |
| 4,058,460 | 11/1977 | Ito | 210/198.2 |
| 4,125,462 | 11/1978 | Latty | 210/500.23 |
| 4,165,219 | 8/1979 | Huber | 73/61.1 C |
| 4,166,747 | 9/1979 | Neely, Jr. | 106/50 |
| 4,183,811 | 1/1980 | Walch et al. | 210/23 R |
| 4,207,188 | 6/1980 | Tsuda et al. | 210/198 C |
| 4,214,020 | 7/1980 | Ward et al. | 427/296 |
| 4,216,083 | 8/1980 | Dale | 210/635 |
| 4,232,811 | 11/1980 | Trask | 428/389 |
| 4,234,652 | 11/1980 | Vanoni et al. | 428/296 |
| 4,268,279 | 5/1981 | Shindo et al. | 55/16 |
| 4,293,418 | 10/1981 | Fuji et al. | 210/321.1 |
| 4,315,819 | 2/1982 | King et al. | 210/321.3 |
| 4,329,383 | 5/1982 | Joh | 428/30 |
| 4,335,017 | 6/1982 | Miles | 210/656 |
| 4,335,226 | 6/1982 | Muller et al. | 525/281 |
| 4,336,161 | 6/1982 | Rosevear et al. | 252/428 |
| 4,376,095 | 3/1983 | Hasegawa | 422/46 |

(List continued on next page.)

FOREIGN PATENT DOCUMENTS 55-18244  2/1980  Japan ................. 210/198.2

OTHER PUBLICATIONS

Caldwell, "Reversible Immobilization of Enzymes to Hydrophobic Agarose Gel", Biotech. and Bioeng., 18 pages, 433–438 (1976).

Yon, "Protein Chromatography on Adsorbents with Hydrophobic and Ionic Group", Biochem J (1975), vol. 151, pp. 281–290.

Mikes Laboratory Handbook of Chromatographic and Allied Methods, 1979, pp. 400–405 and 392–395 and 415–416.

(List continued on next page.)

Primary Examiner—Ernest G. Therkorn
Attorney, Agent, or Firm—K. A. Genoni; B. H. Davidson; J. M. Brown

[57] ABSTRACT

Liquid chromatography separations of solutes are achieved using porous hollow fibers. The pores of the hollow fibers immobilize a solute-absorbing phase (preferably organic) which has a greater absorbance affinity towards at least one solute in a mixture of solutes. By passing the solute mixture through the central lumen of the hollow fibers, chromatographic separation are realized due to the greater retention time of that solute with which the immobilized phase has greater absorbance affinity. The immobilized phase may be a liquid organic which may contain a surfactant so as to form reversed micelles or it may be in the form of a polymeric gel. Separations of biological species (e.g., proteins) may thus be accomplished by means of the present invention.

17 Claims, 3 Drawing Sheets

U.S. PATENT DOCUMENTS

| | | | |
|---|---|---|---|
| 4,405,688 | 9/1983 | Lowery et al. | 428/398 |
| 4,415,631 | 11/1983 | Schutijser | 428/305 |
| 4,424,127 | 1/1984 | Roeraade | 210/198.2 |
| 4,432,875 | 2/1984 | Wrasidlo et al. | 210/500.2 |
| 4,448,687 | 5/1984 | Wang | 210/500.2 |
| 4,451,374 | 5/1984 | Peterson et al. | 210/656 |
| 4,474,664 | 10/1984 | Stevens et al. | 210/656 |
| 4,486,312 | 12/1984 | Slingsby et al. | 210/656 |
| 4,512,896 | 4/1985 | Gershoni | 210/635 |
| 4,541,981 | 9/1985 | Lowery et al. | 264/209.1 |
| 4,544,485 | 10/1985 | Pinkerton et al. | 210/502.1 |
| 4,549,965 | 10/1985 | Davis | 210/635 |
| 4,557,955 | 12/1985 | Walch et al. | 428/35 |
| 4,604,205 | 8/1986 | Ayers | 210/497.2 |
| 4,634,530 | 1/1987 | Kuder et al. | 210/500.23 |
| 4,654,265 | 3/1987 | Kamei et al. | 428/398 |
| 4,657,742 | 4/1987 | Beaver | 422/240 |
| 4,670,341 | 6/1987 | Lundsager | 428/372 |
| 4,675,104 | 6/1987 | Rai et al. | 210/198.2 |
| 4,678,813 | 7/1987 | Itoh et al. | 521/61 |
| 4,689,267 | 8/1987 | Takamizawa et al. | 428/376 |
| 4,708,799 | 11/1987 | Gerlach et al. | 210/500.23 |
| 4,714,555 | 12/1987 | Shibata | 210/635 |
| 4,715,105 | 12/1987 | Beaver | 29/419 G |
| 4,717,479 | 1/1988 | Itoh et al. | 210/490 |
| 4,731,260 | 3/1988 | Balding et al. | 427/238 |

OTHER PUBLICATIONS

Kent E. Goklen and T. Alan Hatton, "Protein Extraction Using Reverse Micelles", Biotechnology Progress, Mar. 1985 (vol. 1, No. 1), pp. 69–74.

Kent E. Goklen and T. Alan Hatton, "Liquid–Liquid Extraction of Low Molecular–Weight Proteins by Selective Solubilization in Reversed Micelles", Separation Science and Technology, 22(2 & 3), 831–841, 1987.

Lise Dahuron, E. L. Cussler, "Protein Extractions with Hollow Fibers", reprinted from AIChE Journal, Jan. 1988, vol. 34, No. 1, pp. 130–136.

Richard F. Meyer et al., "Theory of Multicapillary Columns for HPLC", Journal of Chromatographic Science, vol. 21, Oct. 1983, pp. 433–438.

High Tech Separation News, vol. 1, No. 5, p. 5 (Oct. 1988).

K. L. Loewenstein, "Conversion of Glass into Glass Fibre", The Manufacturing Technology of Continuous Glass Fibres, 1973, pp. 90–91.

"The Making, Shaping and Treating of Steel", Seamless Steel Tubular Products, Section 5, pp. 890–921.

Chuichi Hirayama et al., "High–Speed Aqueous Gel Permeation Chromatography Using a Poly(Vinyl Alcohol) Hollow Fibre", 1986, Elsevier Science Publishers B.V.

Stephen J. Gibbs and Edwin N. Lightfoot, "Scaling Up Gradient Elution Chromatography", Ind. Eng. Chem. Fundam., vol. 25, No. 4, 1986.

Skoog et al., "Fundamentals of Analytical Chemistry", pp. 639–671 (1976).

(COMPARATIVE)

LIQUID CHROMATOGRAPHY USING MICROPOROUS HOLLOW FIBERS

FIELD OF THE INVENTION

The present invention relates to liquid chromatography. In specific embodiments, the invention relates to novel methods and devices which effect liquid chromatography using microporous hollow fibers.

BACKGROUND AND SUMMARY OF THE INVENTION

High performance liquid chromatography is a well known method of separating solute species in dependence upon the differential absorption/desorption between different solute species. Typically, a liquid carrier (in which the solute species to be separated are present) is passed through a column packed with separation media (e.g., solid or gel particles). This separation media, in effect, increases the residence time of one (or more) solute species in the liquid carrier (which is inert to the solute species) relative to one (or more) other solute species in the liquid carrier (i.e., due to the greater rate of absorption/desorption of the one solute species relative to the other solute species). Due to the increased residence time of the one solute species in the column, there will be a time when an essentially pure mixture of carrier liquid and the other solute species will be present at the discharge of the column—that is, the one and other solute species will b separated.

With the recent advent of commercial manufacture of biological species (e.g., proteins), however, the conventional liquid chromatography technique of using packed particle beds has proven to be an inefficient means of separating one species from another with high resolution. This inability of packed particle chromatography columns can be attributed generally to the high pressure drops which are experienced and which lead to lesser flow rates of the liquid carrier through the column (thereby leading to lesser rate of production of the desired biological species). In addition, the very stringent control over particle size, the uniformity of the particles and the manner in which such particles fill the column contribute to increased costs which, in general, cannot be tolerated on a commercial scale. Hence, the conventional packed particle technique for liquid chromatography, while being adequate for analytical purposes on a small scale, is inadequate for separating solute species (particularly biological species) on a commercial scale.

Recently, it has been proposed to employ hollow fibers for liquid chromatography. The geometry of such hollow fibers provides an attractive alternative to particles in terms of lesser pressure drop through the column, and the lower cost of hollow fibers (relative to uniform particles) which provides attractive economies of scale and thus may allow commercially viable liquid chromatography systems to be achieved.

One prior proposal in this regard employs a tube packed to between 60 to 100 percent of the tube's theoretical packing density with generally parallel aligned fibers so as to provide the means to perform liquid chromatography. See, U.S. Pat. No. 4,657,742 issued on Apr. 14, 1987 to Richard P. Beaver. The fibers in U.S. Pat. No. 4,657,742 are preferably glass fibers which may be solid or they may be solid fibers that have been rendered porous. Alternately, the fibers may be hollow fibers having solid walls or hollow fibers whose walls have been treated so as to render them porous. The process for packing the tube with a high density of fibers is also said to be applicable to fibers other than glass, for example, cellulosic and organic fibers (see column 10, lines 10–13 of USP 4,657,742).

In Japanese Publication No. 55-18244, there is disclosed a hollow fiber which is suitable for use in liquid chromatography. The hollow fiber disclosed therein includes an external liquid-impermeable skin layer and an internal (i.e., adjacent the lumen of the fiber) porous layer. The liquid-impermeable layer apparently allows liquid chromatography to proceed with increased pressure within the internal lumen of the fiber without carrier liquid "breakthrough" to the external side of the fiber.

While the above-mentioned proposals for liquid chromatography may provide some improvement over the conventional packed particle columns used in liquid chromatography applications, there still exists a need in this art for greater solute separation resolution on a commercially viable scale—that is a liquid chromatography system which is adapted to separate a greater amount of solute species per unit time as compared to conventional liquid chromatography techniques. It is towards achieving such needed improvements that the present invention is directed.

According to the present invention, microporous hollow fibers (preferably polyolefinic fibers which are normally hydrophobic) are employed as the means to immobilize, within the micropores of the fiber, a stationary phase having a greater affinity to at least temporarily absorb at least one solute species relative to at least one other solute species. Thus, when a liquid carrier containing the solute species to be separated is passed through the central lumen of the hollow fiber, at least one of the solute species will have a greater residence time within the hollow fiber (i.e., due to its affinity to be at least temporarily absorbed by the immobilized phase within the fiber's micropores), thereby causing the solute species to be separated at the outlet end of the fiber—that is, the solute species with which the immobilized phase has a lesser affinity for absorption will appear in essentially "pure" form (but carried by the carrier liquid) before the solute species with which the immobilized phase has a greater absorption affinity.

Preferably, the immobilized phase within the fiber's micropores is organic since it more easily "wets" the normally hydrophobic hollow fibers (i.e., so that the organic phase fills completely the micropores of the hollow fiber). The immobilized phase may thus be an organic liquid or a gel, with the particular chemical composition of the immobilized phase being selected in dependence upon a number of factors, including its compatibility with the material of the hollow fiber and/or its compatibility with the solutes to be separated, and/or its absorption/desorption affinity for particular solute species of interest to be separated.

Therefore, according to the present invention, a commercially viable alternative to prior liquid chromatography techniques is provided. This advantage, as well as others, will become more clear after careful consideration is given to the following detailed description of the preferred exemplary embodiments thereof.

BRIEF DESCRIPTION OF THE ACCOMPANYING DRAWINGS

Reference will hereinafter be made to the accompanying drawings wherein like reference numerals throughout the various FIGURES denote like structural elements, and wherein.

DETAILED DESCRIPTION OF THE PREFERRED EXEMPLARY EMBODIMENTS

Figure 1:
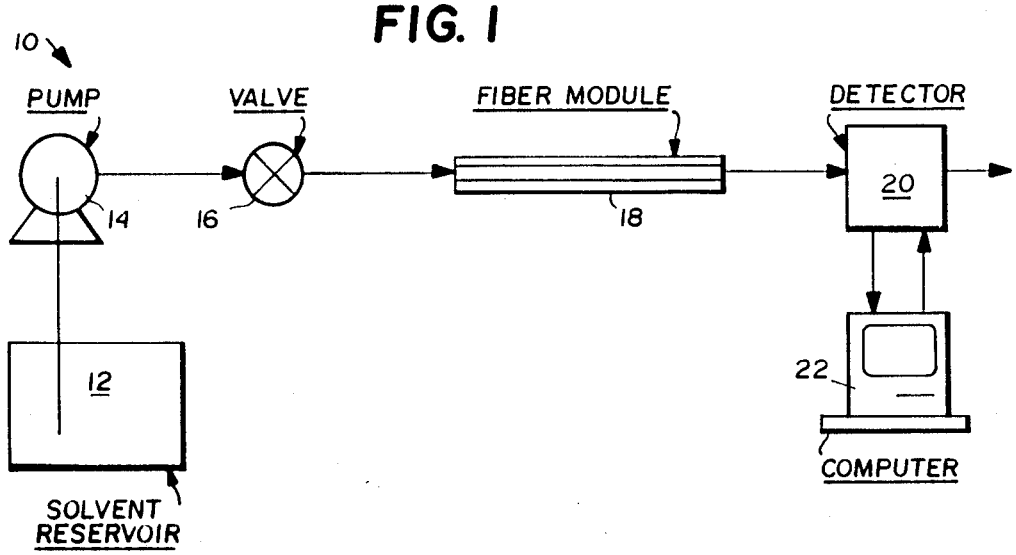
FIG. 1 is a schematic view of a liquid chromatography system utilized in the Examples below.

The novel liquid chromatographic columns of the present invention include a number of microporous hollow fibers. Although any suitable microporous hollow fiber may be employed in the practice of this invention, it is presently preferred to use microporous, normally hydrophobic polyolefin (e.g., polypropylene or polyethylene) hollow fibers arranged generally parallel to one another in a closely packed relationship within an outer shell structure.

The preferred hollow fibers employed in this invention are those of the type made using the "up-spinning" technique disclosed in U.S. Pat. Nos. 4,405,688 and 4,451,981, each in the name of James J. Lowery et al, and each being expressly incorporated hereinto by reference. Briefly, non-porous precursor hollow fibers are produced according to the techniques disclosed in these prior patents by melt spinning the precursor fibers in a substantially vertically upward direction (i.e., up-spinning). The thus melt spun hollow precursor fibers are then spin-oriented while subjecting them to a symmetrical quenching step using a hollow annular structure surrounding the precursor fiber which has one or more openings on its inner surface that distribute the quenching medium against the precursor fiber in a substantially uniform manner. The thus formed hollow precursor fiber may then be heat annealed by, for example, subjecting the non-porous precursor hollow fiber to a temperature of between about 5° C. to 100° C. for a time period of at least a few seconds (e.g., from a few seconds up to about 24 hours, preferably between about 30 minutes to about 2 hours).

The finished microporous hollow fibers will possess an average inner diameter in the range of from about 5 to about 1500 microns, and preferably in the range of from about 70 to about 1500 microns. The fibers are moreover characterized by a substantially uniform internal diameter (I.D.), for example, a coefficient of variation in inner diameter through a cross-section taken perpendicular to the axis of the fiber of less than about 8%, preferably less than about 5%, and more preferably less than about 3%.

The pores of the preferred microporous hollow fibers are essentially interconnected through tortuous paths which may extend from one exterior surface or surface region to another, i.e., open-celled. Further, the pores of the preferred microporous hollow fibers of the present invention are microscopic, i.e., the details of the pore configuration or arrangement are described only in terms of microscopic dimensions. Thus, the open cells or pores in the fibers are smaller than those which can be measured using an ordinary light microscope, because the wavelength of visible light, which is about 5,000 Angstroms, is longer than the longest planar or surface dimension of the open cell or pore. The pore size of the microporous hollow fibers may be defined by using electron microscopy techniques which are capable of resolving details of pore structure below 5,000 Angstroms or by mercury porosimitry techniques.

The average effective pore size of the microporous hollow fibers useable in the practice of this invention is preferably between 50 to 2000 Angstroms, and more typically between 100 to 1000 Angstroms. By "average effective pore size" is meant the smallest dimension of a pore which would allow a generally spherical particle of that same dimension to pass therethrough. The pores generally have an elongated shape with a width of from 50 to 2000 Angstroms, and a length of from 500 to 10,000 Angstroms. Hence, the "average effective pore size" of the preferred microporous hollow fibers will usually be determined by the width dimension of the pores. These pores will, moreover, be fairly uniform around the circumference of the fiber. For example, the preferred microporous hollow fibers will exhibit an average ratio of the maximum pore density to the minimum pore density around the circumference of the fiber of less than about 3:1, and usually less than about 2:1.

Microporous hollow fibers of the type described above are commercially available from Hoechst Celanese Corporation, Separations Products Division, Charlotte, N.C. under the registered trademark CELGARD®.

The microporous hollow fibers are preferably a part of a module having an inlet end and an outlet end. The module includes a number (e.g., from a few hundred to many thousand) of hollow fibers of predetermined length arranged substantially parallel to one another within the central space of a generally tubular shell structure (e.g., glass or metal tubes). The individual fibers are positionally retained within the outer shell structure by means of suitable potting compounds (e.g., epoxy resins). Modules of this type are commercially available in a wide range of sizes and capacities. For example, one particular microporous hollow fiber module which may be satisfactorily employed in the practice of the present invention is commercially available from Hoechst Celanese Corporation, Separations Products Division, Catalog No. 50101060. This module has 27,000 CELGARD® microporous hollow fibers of 100 μm internal diameter. Other suitable microporous hollow fiber modules may, however, be used for the chromatographic separations according to the present invention.

The phase that is immobilized within the micropores of the hollow fibers is preferably organic and can be either a liquid or a solid (e.g., a polymeric gel). The selection of any particular immobilized phase depends upon a number of factors including the particular solute(s) to be separated, its pH dependency, and/or its compatibility and wettability with respect to the microporous hollow fibers in the chromatographic module.

Important to the present invention is that the immobilized phase be selected so that it exhibits a greater absorption affinity towards at least one solute species as compared to its absorption affinity towards at least one other solute species. That is, the immobilized phase must have a differential partition coefficient "K" as between one and another of the solute species intended to be separated. In this regard, refer to Skoog et al, "Fundamentals of Analytical Chemistry", pages 639–671 (1976).

The immobilized phase is most preferably an organic liquid. Virtually any suitable organic liquid may be employed in the practice of this invention, the selection of any particular organic liquid again depending upon at least some of the factors enumerated above. For example, when employing polypropylene microporous hollow fibers, the organic liquid is one which is capable of "wetting" the fiber. Such organic liquids will preferably be water immiscible and/or will exhibit a surface tension of less than about 50 dynes, and more preferably less than about 35 dynes.

By way of example only, organic liquids which may be employed in the practice of the present invention includes aldehydes, ketones (e.g., methyl ethyl ketone, methyl isobutyl ketone, methyl cyclohexanone, dimethyl cyclohexanone), esters (e.g., cyclohexyl acetate, furfuryl acetate, amyl acetate), ethers (e.g., 2-chloro-2-methoxy diethyl ether, diisopropyl ether), aliphatic and aromatic hydrocarbons (e.g., hexane, dodecane, and benzene, toluene, respectively), organic alcohols (e.g., iso-butanol, butanol-pentanol, octanol, dodecanol, methyl cyclohexanol, 2-ethyl bexanol), and carboxylic acids (e.g., octanoic acid, naphthenic acids). Other organic liquids may also be employed, such as, tributyl phosphate, trioctyl phosphate, trioctyl phosphine oxide, phosphonic acid esters, dimethyl phthalate, diethyl oxalate, aryl sulfonic acids, hydroxyoximes, oxine derivatives, $\beta$-diketones, alkarylsulfonamides, and primary, secondary, tertiary and quartenary amines, to name just a few.

When used to separate biological species, for example proteins, the immobilized liquid organic phase most preferably includes nanometer scale droplets of an aqueous solution stabilized in an apolar environment by the presence of surfactant at the interface—that is, so-called "reverse micelles". In this regard, see Goklen et al, "Protein Extraction Using Reverse Micelles", Biotechnology Progress, Vol. 1, No. 1, pp. 69–74 (March, 1985) and Goklen et al, "Liquid-Liquid Extraction of Low Molecular-Weight Proteins by Selective Solubilization in Reversed Micelles", Separation Science and Technology, 22(2–3), pp. 831–841 (1987), the entire content of each of these publications being expressly incorporated hereinto by reference. These reverse micelles exhibit a certain electrostatic charge which is pH dependent (i.e., changes with a change in pH) and Which can therefore be utilized to solubilize a protein of an opposite charge. In the context of the present invention therefore, when the solutes to be separated are proteins and the immobilized organic phase within the micropores of the hollow fiber include such reverse micelles, the pH of the mobile phase is selected so that the reverse micelle will solubilize a particular protein of different electrostatic charge. After the other protein of substantially like electrostatic charge has been separated (i.e., since it is not solubilized by means of the reverse micelles), the solubilized protein can be eluted by changing the pH of the mobile phase (which will affect the electrostatic charge of the reverse micelle).

Any surfactant capable of forming reversed micelles in an apolar environment may be used in the practice of this invention. Preferably, the surfactant will bedidodecylsulfosuccinate (Aerosol-OT), or a cationic amine, for example, hexadecyltributyl ammonium chloride.

When organic liquids are employed as the immobilized phase according to the present invention, the micropores of the hollow fibers are most conveniently filled by placing a small volume of the organic liquid at the top of a column containing a number of hollow fibers and allowing this liquid to wick into the fibers thereby wetting the same (i.e., filling the micropores).

It is important that all of the microporous fibers in the module be wet evenly with the organic liquid. When using normally hydrophobic microporous hollow fibers of polyolefin (e.g., polypropylene) as above described, the appearance of the fibers will change from a characteristic normal opaque to translucent when wet with the organic liquid. The presence of unfilled micropores in the hollow fiber is therefore readily determined visually by inspecting the fibers for opaque regions surrounded by translucent regions. In order to be usable in the practice of the present invention, all of the fibers in the module must be translucent indicating that all micropores have bee uniformly filled.

Another class of organic phases which may be immobilized in the micropores of the hollow fiber are so-called polymeric gels modified with affinity ligands. The polymeric gels may, for example, be polyacrylamide, cross-linked polystyrene, starch (e.g., aqueous Dextrin commercially available from Sephadex Corporation and Pharmacia Corporation), or cross-linked silanes, with polyacrylamide being presently preferred.

When employing polyacrylamide as the immobilized gel phase within the micropores of the hollow fibers, it is preferred to wet the fiber (i.e., fill the micropores) with a liquid acrylamide monomer, modified to take affinity ligands, in a manner similar to that described above with respect to other liquid organics. Liquid acrylamide monomers so modified are very well known in and of themselves and are available from a number of commercial sources, for example, from Pharmacia and Biorad Corporations. The selection of any particular acrylamide monomer (i.e., one having particular affinity ligands) that is employed in the practice of the present invention will, of course, depend to a large extent upon the particular solute species intended to be separated. Suffice it to say here, that those skilled in this art are entirely capable of selecting any particular acarylamide monomer with an affinity ligand suitable to achieve separation of solute species of particular interest. When the acrylamide monomer has been immobilized within the hollow fiber micropores, polymerization of the acrylamide monomer may then be accomplished in situ.

Once the organic liquid or gel has been immobilized within the micropores of the hollow fiber, chromatographic separations can then be accomplished, for example, using the system 10 shown in accompanying FIG. 1. As is seen, the system 10 includes a solvent reservoir 12 which contains pure liquid solvent. For most solutes, an aqueous solution is employed for the solvent. The solvent is pumped from the reservoir 12 via a suitable pump 14, through an injector valve 16 into the inlet of a hollow fiber module 18 as above described. The solute species may thus be injected at time $t_0$ into a stream of pure solvent via the injector valve 16 and travel on to the inlet of the hollow fiber module 18. The stream exiting the module 18 at time $t_1$ later than time $t_0$ may be analyzed via any suitable analytical instrument, for example, an ultraviolet visible detector 20 which outputs signals to a suitable microprocessor 22 so as to generate graphs and/or otherwise put the collected data in human-readable form. Thereafter the stream may be passed to a collection site for collecting the separated solutes for further processing and/or purification (i.e., solvent removal).

The invention will be further described by way of the following Examples which are intended to be illustrative only and non-limiting.

EXAMPLE I

Figure 2:
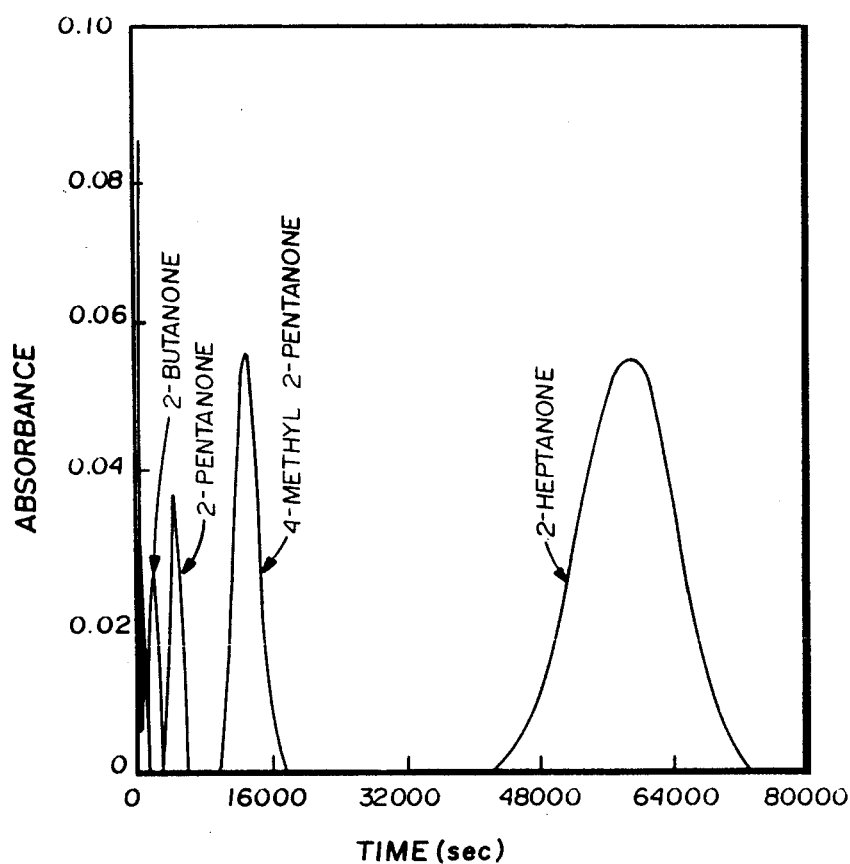
FIG. 2 is a representative plot of absorbance versus time showing the separation resolution achieved according to EXAMPLE I below.

An aqueous solution of solutes 2-butanone, 2-pentanone, 2-hexanone, and 2-heptanone in equal amounts was injected into a microporous hollow fiber module wherein the fibers were wet with a solution of 50% trioctylphosphate/50% dodecane. The module contained 420 microporous polypropylene hollow fibers (CELGARD ®), each 60 cm long having an internal diameter of 100 μm and a wall thickness of 30 μm. Accompanying FIG. 2 shows the results of the chromatographic separation of the solutes.

EXAMPLE IIA

Example I was repeated using a module having 420 microporous polypropylene hollow fibers, each 60 cm in length and an internal diameter of 100 μm The solutes employed in this EXAMPLE II were 2-butanone, methyl-i-butanone, 2-pentanone, cyclohexanone, 2-heptanone, and 4-heptanone with the immobilized phase being 50% trioctylphosphate/50% dodecane. The results appear below in Table A.

TABLE A

| Column[a] | Solute | length/ velcosity (1/v,sec[b]) | residence time ($t_R$,sec) | band width ($\nabla^2$,sec$^2$) |
|---|---|---|---|---|
| 60 cm/ 420/TOP | 2-Butanone | 29.8 | 74.6 | 1,170 |
| | Methyl-i-Butanone | 29.8 | 166.0 | 3,390 |
| | 2-Pentanone | 298 | 176.0 | 3,700 |
| | Cyclohexanone | 29.8 | 139.0 | 3,300 |
| | 2-Heptanone | 29.8 | 2200.0 | 354,000 |
| | 4-Heptanone | 29.8 | 2410.0 | 460,000 |

[a]The first figure given below is the column length l; the second is the number of 100 micrometer fibers, and the abbreviation "TOP" denotes the stationary phase consisting of 50% trioctylphosphate and 50% dodecane.
[b]Based on a nominal diameter of 100 micrometers.

The above data in Table A demonstrate that mixed solutes can be successfully separated by liquid chromatography in microporous hollow fibers having a liquid organic phase immobilized within the micropores thereof.

EXAMPLE IIB

Example IIA was repeated using the columns and solutes identified in Table B, below. As can be seen from the data of Table B, effective solute separations are possible.

TABLE B

| Column[a] | Solute | length/ velcosity (1/v,sec[b]) | residence time ($t_R$,sec) | band width ($\nabla^2$,sec$^2$) |
|---|---|---|---|---|
| 61 cm/480/ 12 OH | m-Nitrophenol | 37.0 | 952.0 | 121,000 |
| | " | 88.8 | 2330.0 | 44,300 |
| | p-Nitrophenol | 65.8 | 1430.0 | 322,000 |
| | " | 140.0 | 3290.0 | 899,000 |
| | Uracil | 32.1 | 43.4 | 37 |
| | " | 210.0 | 288.0 | 2,160 |
| 21 cm/480/ 12 OH | m-Nitrophenol | 10.3 | 250 | 14,900 |
| | " | 43.8 | 1070 | 104,000 |
| | 4-Heptanone | 10.9 | 426 | 27,700 |
| | " | 273.0 | 10,400 | 4.23 × 10$^6$ |
| | 2-Pentanone | 30.0 | 106 | 4,600 |
| | " | 97.6 | 343 | 23,400 |
| | " | 167.0 | 614 | 68,230 |
| | Phenol | 17.6 | 100 | 7,020 |
| | " | 25.5 | 139 | 8,290 |
| | " | 75.5 | 437 | 48,900 |
| | o-Nitrophenol | 29.7 | 20.4 | 14 |
| | " | 118.0 | 79.4 | 157 |

[a]The first figure given below is the column length l; the second is the number of 100 micrometer fibers, and the abbreviation "12 OH" denotes the stationary liquid phase consisting of 75% dodecanol and 25% dodecane.
[b]Based on a nominal diameter of 100 micrometers.

EXAMPLE III (COMPARATIVE)

Example I was repeated except that a liquid organic phase was not present in the micropores of the hollow fibers. Thus, the microporous hollow fibers employed in this EXAMPLE III did not have an immobilized phase within the fibers' micropores. The results appear in the graph of FIG. 3.

Figure 3:
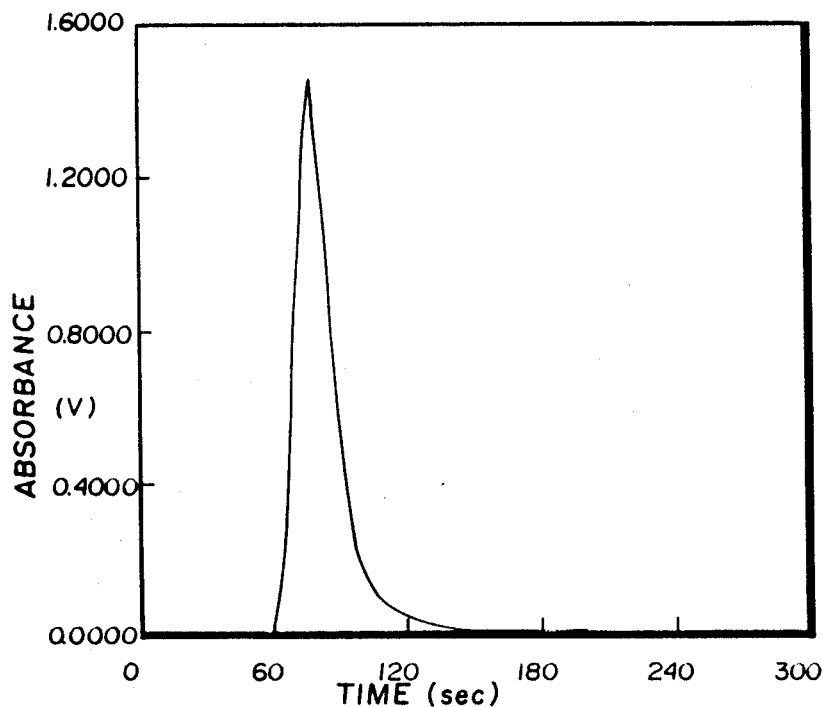
FIG. 3 is a plot of absorbance versus time for the same solutes shown in FIG. 2 but without using an organic phase immobilized in the micropores of the hollow fiber (i.e., according to EXAMPLE III, below)

It will immediately be apparent from FIG. 3 that no separation of the solute species occurred (i.e., since only a single peak is present). Note also the different time scale as between FIGS. 2 and 3, the latter being significantly shorter than that employed in the former. Hence, on the same time scale as that employed in FIG. 2, the solutes would appear in FIG. 3 as a sharp peak near the y-axis. This data indicates that the "empty" micropores were incapable of separating the solutes one from another.

EXAMPLE IV

The efficacy of liquid chromatography using an immobilized organic solution of reversed micelles was examined. This EXAMPLE IV employed a module 60 cm in length, containing 480 microporous polypropylene hollow fibers (CELGARD ®) of 100μm internal diameter. The mobile phase consisted of an aqueous solution of the proteins myoglobin and cytochrome-c in equal masses buffered at a pH of 6. The immobilized phase consisted of dodecane as the solvent and sodium di-dodecylsulfosuccinate as the reverse micelle-forming surfactant.

Figure 4:
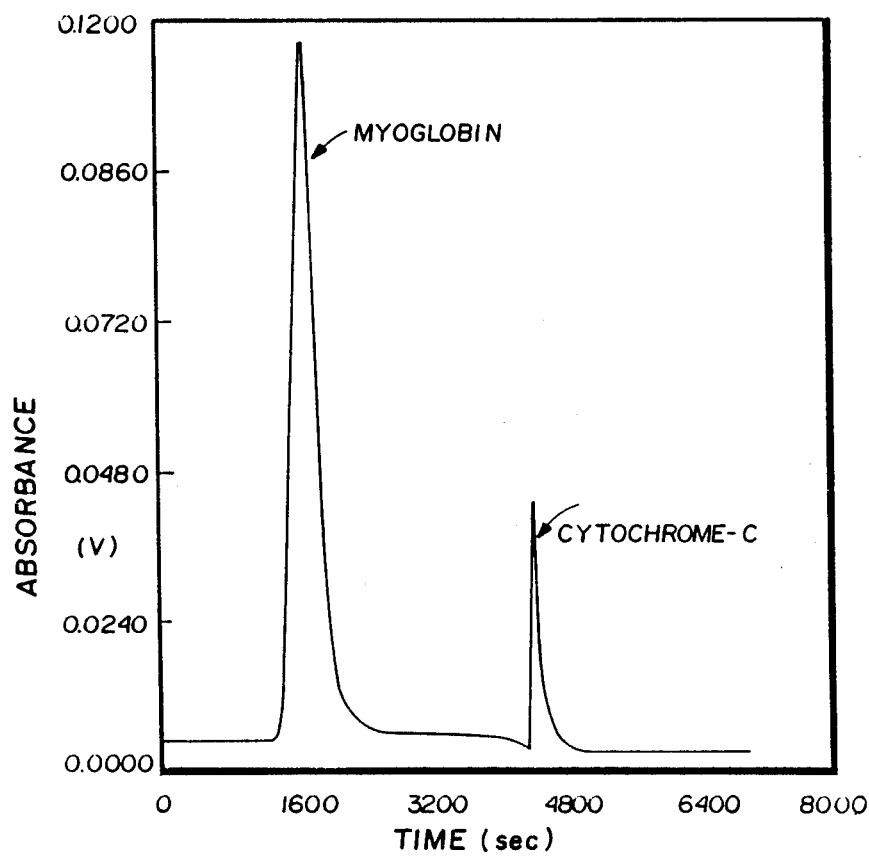
FIG. 4 is a plot of absorbance versus time for separation attained according to EXAMPLE IV below.

The mobile aqueous phase containing the proteins and buffered at a pH of 6 was injected into an aqueous stream which passed through the central lumens of the hollow microporous fibers in the module. At a pH of 6, the cytochrome-c exhibits a positive charge and was therefore retained in the micelles in the immobilized organic phase. The myoglobin, of negative charge at pH of 6, passed through the module at the mean residence time of the mobile phase. After the myglobin had passed through the module, the pH of the mobile phase was changed to 10. At this higher pH, the cytochrome-c has a negative charge, causing it to be eluted from the module. Thus, a high resolution separation occurred as between the cytochrome-c and the myoglobin as is shown in FIG. 4.

EXAMPLE V

Figure 5:
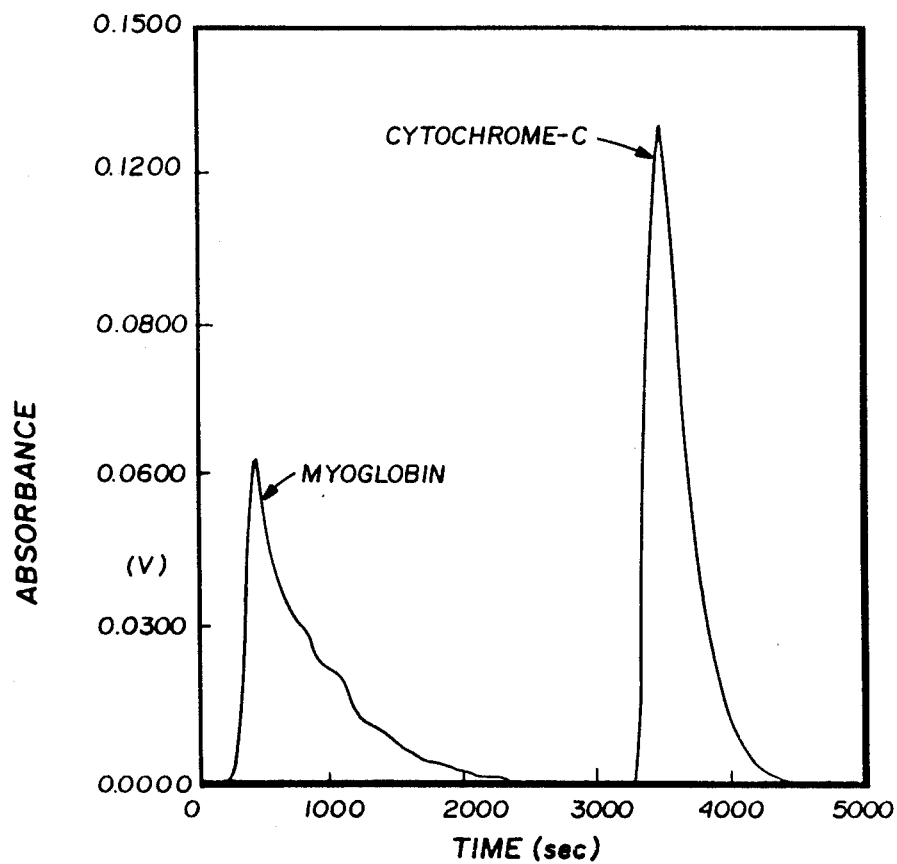
FIG. 5 is a plot of absorbance versus time for the separation attained according to EXAMPLE V below.

EXAMPLE IV was repeated, except that a larger commercial scale module (Catalog No. 50101060, Hoechst Celanese Corporation, Separations Products Division, Charlotte, N.C.) was employed. The module used in this EXAMPLE V was 22 c long, and contained 27,000 microporous hollow fibers (CELGARD ®) of 100 μm internal diameter. The results of the chromatographic separation achieved by this EXAMPLE V are shown in FIG. 5.

The above Examples demonstrate that the present invention achieves solute separation using microporous hollow fibers. Moreover, as Example V shows, the present invention can be "scaled-up" to provide a viable technique for separating commercially important solute species.

However, while the invention has been described in connection with what is presently considered to be the most practical and preferred embodiment, it is to be understood that the invention is not to be limited to the disclosed embodiment, but on the contrary, is intended to cover various modifications and equivalents included within the spirit and scope of the appended claims.

I claim:

1. A liquid chromatography method for separating at least solute species A and B comprising the steps of:
   (a) immobilizing, within pores of a number of open celled, microporous hollow fibers having an average pore size of less than 5,000 Å, an inner diameter of from about 5 to about 1500 microns, a coefficient of variation in inner diameter of less than about 8%, and an average ratio of maximum pore density to minimum pore density around the circumference of the fiber of less than about 3:1, a solute-absorbing phase having a greater affinity for absorbing-/desorbing solute species A as compared to solute species B;
   (b) passing a carrier liquid stream through the lumens of said microporous hollow fibers; and then
   (c) injecting a sample mixture comprised of solute species A and B into said carrier liquid stream so that a liquid mixture comprised of said carrier liquid and said solute species A and B passes through the lumens of said hollow fibers;
   (d) allowing said solute species A to be absorbed preferentially by said immobilized solute-absorbing phase so that a first mixture comprised essentially of the carrier liquid and solute species B is initially discharged from said hollow fiber lumens; and then
   (e) allowing the solute species A to desorb into said carrier liquid stream so as to form a second mixture comprised essentially of the carrier liquid and the solute species A which is discharged from said hollow fiber lumens subsequent to the discharge of said first mixture comprised essentially of the carrier liquid and solute species B, whereby solute species A and B are separated from said sample mixture thereof.

2. A method as in claim 1, wherein said solute-absorbing phase is organic and said carrier liquid is aqueous.

3. A method as in claim 2, wherein said immobilized organic phase is liquid.

4. A method as in claim 2, wherein said immobilized organic phase is a polymeric gel.

5. A method as in claim 4, wherein said polymeric gel is selected from the group consisting of polyacrylamide, polystyrene, starch, and cross-linked silanes.

6. A method as in claim 1, wherein said average pore size of said microporous hollow fiber is between 50 to 2,000 Angstroms.

7. A liquid chromatography method comprising the steps of:
   (a) providing a liquid chromatography module having an inlet and an outlet, and a number of open-celled microporous hollow fibers having lumens which establish fluid communication between said module inlet and outlet, wherein said number of microporous hollow fibers are arranged within said module generally parallel to one another between said module inlet and outlet, and have an average pore size of less than 5,000 Å, an inner diameter of from about 5 to about 1500 microns, a coefficient of variation in inner diameter of less than about 8%, and an average ratio of maximum pore density to minimum pore density around the circumference of the fiber of less than about 3:1;
   (b) uniformly wetting each of said microporous hollow fibers with an organic phase having an affinity for absorbing/desorbing one solute species as compared to another solute species so that said organic phase is immobilized within the open-celled micropores of said hollow fibers;
   (c) passing a carrier liquid stream through said lumkens of said hollow fibers;
   (d) injecting into said carrier liquid stream at time $t_0$ a solution containing a sample mixture of at least said one and another solute species, and thereby allowing a stream comprised of said carrier liquid and said one and another solute species to pass through the lumens of said microporous hollow fibers in a direction from said module inlet towards said module outlet during a time interval from time $t_0$ to time $t_1$;
   (e) allowing, during said time interval from time $t_0$ to time $t_1$, said one solute species to be temporarily absorbed into said immobilized organic phase to thereby allow said another solute species to pass through said lumens of said hollow fibers without substantial absorption into said immobilized organic phase so that at time $t_1$, a first mixture comprised essentially of said carrier liquid and said another solute species is discharged from said module outlet; and then
   (f) allowing said one solute species to be desorbed into said carrier liquid stream so that a second mixture comprised essentially of said carrier liquid and said one solute species is discharged from said module outlet at a time $t_2$ later than time $t_1$, whereby said one and another solute species are separately discharged from said module outlet.

8. A method as in claim 7, wherein said solute-absorbing phase is organic and said carrier liquid is aqueous.

9. A method as in claim 8, wherein said immobilized organic phase is liquid.

10. A method as in claim 8, wherein said immobilized organic phase is a polymeric gel.

11. A method as in claim 10, wherein said polymeric gel is selected from the group consisting of polyacrylamide, polystyrene, starch, and cross-linked silanes.

12. A method as in claim 8, wherein said average pore size of said microporous hollow fiber is between 50 to 2,000 Angstroms.

13. A process for separating at least one biological species from another biological species, comprising the steps of:
   (a) immobilizing, within the micropores of a number of open-celled microporous hollow fibers having an average pore size of less than 5,000 Å, an inner diameter of from about 5 to about 1500 microns, a coefficient of variation in inner diameter of less than about 8%, and an average ratio of maximum pore density to minimum pore density around the circumference of the fiber of less than about 3:1, an organic phase which includes a surfactant capable of forming reversed micelles within said organic phase;

(b) buffering an aqueous phase comprised of a mixture of one and another biological species to an initial pH whereby one of said biological species exhibits a negative charge and said another biological species exhibits a positive charge;

(c) passing said buffered aqueous phase through lumens of said hollow fibers and allowing essentially all of said one biological species to be absorbed within said reversed micelles of said immobilized phase while said another biological species passes on to an outlet end of said hollow fibers so that a stream comprised essentially of all said another biological species is discharged from said outlet end of said hollow fibers, whereby said one and another biological species are separated; and then subsequently (d) eluting said absorbed one biological species after said another biological species has been discharged from said outlet end of said hollow fibers, said step of eluting said absorbed one biological species including the steps of;

(i) buffering a carrier liquid to a pH different from said initial pH of said aqueous phase and to a pH which is sufficient to effect a charge reversal of said one biological species from a negative charge to a positive charge; and then (ii) passing the buffered carrier liquid through said lumens of said hollow fibers to effect said charge reversal of said one biological species and to thereby cause said one biological species to be eluted from said micropores into said carrier liquid.

14. A process for separating at least one biological species from at least one other biological species, comprising the steps of:

(a) immobilizing, within the micropores of a number of microporous hollow fibers, an organic phase which includes a surfactant capable of forming reversed micelles within said organic phase; and then (b) injecting a mixture of said one and other biological species into a stream of aqueous carrier liquid, buffered to an initial pH such that said one biological species exhibits a negative charge and said other biological species exhibits a positive charge;

(c) passing said carrier liquid and injected one and other biological species through lumens of said hollow fibers and allowing said one biological species to be absorbed within said reversed micelles of said immobilized phase while said other biological species passes on to an outlet end of said hollow fibers so that a liquid mixture comprised of said carrier liquid and essentially all said other biological species is discharged from said outlet end of said hollow fibers;

(d) changing the pH of an additional quantity of said carrier liquid to a pH which is different from said initial pH of said carrier liquid and said injected biological species passed through said lumens of said hollow fibers according to step (c), and which is sufficient to cause a charge reversal of said one biological species;

(e) passing said additional quantity of carrier liquid, having said different pH according to step (d), through said lumens of said hollow fibers and then (f) eluting said one biological species from said organic phase and into said additional quantity of carrier liquid being passed through said lumens of said hollow fibers according to step (e) by allowing said different pH of said additional quantity of carrier liquid to reverse the charge of said one biological species so that said one biological species is desorbed from said reversed micelles, whereby said one and other biological species are separated.

15. A method as in claim 14, wherein each of said one and other biological species is a protein.

16. A liquid chromatography method comprising the steps of:

(a) immobilizing a polymeric gel, modified to take affinity ligands, in the pores of a number of open-celled microporous hollow fibers having an average pore size of less than 5,000 Å, an inner diameter of from about 5 to about 1500 microns, a coefficient of variation in inner diameter of less than about 8%, and an average ratio of maximum pore density to minimum pore density around the circumference of the fiber of less than about 3:1; and subsequently (b) passing, through the lumens of said porous hollow fibers, an aqueous stream containing a mixture of solutes to be separated, at least one of said solutes in said mixture having a greater affinity to absorption by said immobilized polymeric gel, whereby said at least one solute is separated from other solutes in said mixture, wherein said step (a) includes the steps of:

(i) filling the micropores of said hollow fibers with a liquid monomer of said polymeric gel, and then subsequently (ii) polymerizing said monomer in situ within said micropores of said hollow fibers.

17. A method as in claim 16, wherein said monomer is a liquid acrylamide modified to take affinity ligands.

* * * * *